United States Patent [19]

Schreiber et al.

[11] Patent Number: 5,233,024

[45] Date of Patent: Aug. 3, 1993

[54] **ANTI-IDIOTYPIC MONOCLONAL ANTIBODIES FOR MUCOID *PSEUDOMONAS AERUGINOSA*, THEIR PREPARATION AND USE**

[75] Inventors: John R. Schreiber, Gates Mills, Ohio; Gerald B. Pier, Brookline, Mass.

[73] Assignees: The Brigham & Women's Hospital, Boston, Mass.; Case Western Reserve University, Cleveland, Ohio

[21] Appl. No.: 682,685

[22] Filed: Apr. 9, 1991

[51] Int. Cl.$^5$ .......................... C07K 15/28; C12N 5/12
[52] U.S. Cl. .............................. 530/387.2; 530/388.4; 435/240.27
[58] Field of Search ................ 424/85.8; 530/387.2, 530/388.4; 435/240.27

[56] References Cited

U.S. PATENT DOCUMENTS

| | | | |
|---|---|---|---|
| 4,157,389 | 6/1979 | Homma et al. | 424/92 |
| 4,160,023 | 7/1979 | Homma et al. | 424/87 |
| 4,285,936 | 8/1981 | Pier et al. | 424/180 |
| 4,578,458 | 3/1986 | Pier | 536/123 |
| 4,677,070 | 6/1987 | Larrick et al. | 435/240 |
| 4,693,891 | 9/1987 | Collins et al. | 424/92 |
| 4,834,975 | 5/1989 | Siadak et al. | 424/87 |
| 4,834,976 | 5/1989 | Rosok et al. | 424/87 |
| 4,918,163 | 4/1990 | Young et al. | 530/387 |
| 4,965,068 | 10/1990 | Stephan et al. | 424/87 |
| 4,970,070 | 11/1990 | Raff | 424/87 |

FOREIGN PATENT DOCUMENTS 101039 2/1984 European Pat. Off.

OTHER PUBLICATIONS

Journal of Experimental Medicine, vol. 160, issued Oct. 1984, K. E. Stein et al., "Neonatal Administration of Idiotype or Antiidiotype Primes for Protection Against *Escherichia coli* K13 Infection in Mice", pp. 1001-1011, see the entire document.

Schreiber, J. R., et al., "Anti-Idiotype-induced Lipopolysaccharide-specific Antibody Response to *Pseudomonas aeruginosa*", *The Journal of Immunology*, pp. 188-193 (Jan. 1, 1991).

Schreiber, J. R., et al., "Anti-Idiotype-Induced, Lipopolysaccharide-Specific Antibody Response to *Pseudomonas aeruginosa*", *Journal of Immunology*, vol. 144, pp. 1023-1029 (Feb. 1, 1990).

Pier, G. B., et al., "Opsonophagocytic Killing Antibody to *Pseudomonas aeruginosa* Mucoid Exopolysaccharide in Older Noncolonized Patients with Cystic Fibrosis", *The New England Journal of Medicine*, vol. 317, pp. 793-798 (Sep. 24, 1987).

Dressman, G. R. and Kennedy, R. C., "Anti-Idiotypic Antibodies; Implications of Internal Image-Based Vaccines for Infectious Diseases", *The Journal of Infectious Diseases*, vol. 151, pp. 761-765 (May, 1985).

Westerink, M. A. J., et al., "Development and Characterization of an Anti-Idiotype Antibody to the Capsular Polysaccharide of *Neisseria meningitidis* Serogroup C", *Infection and Immunity*, vol. 56, pp. 1120-1127 (May, 1988).

Percival, D. A., et al., "Anti-Idiotypic Antibody-Induced Protection Against *Clostridium perfringens* Type D", *Infection and Immunity*, vol. 58, pp. 2487-2492 (Aug., 1990).

Garner, C. V., et al., "Immunogenic Properties of *Pseudomonas aeruginosa* Mucoid Exopolysaccharide", *Infection and Immunity*, vol. 58, pp. 1835-1842 (Jun., 1990).

(List continued on next page.)

*Primary Examiner*—Susan L. Futrovsky
*Attorney, Agent, or Firm*—Pearne, Gordon, McCoy & Granger

[57] ABSTRACT

An anti-idiotypic monoclonal antibody, which induces production of mucoid exopolysaccharide-specific antibodies which are opsonic for mucoid *Pseudemonas aeruginosa*. The anti-idiotypic monoclonal antibody is produced by a cell line designated C9F5 and having ATCC accession No. HB10715. The anti-idiotypic monoclonal antibody is useful as a vaccine and for diagnostic purposes.

3 Claims, No Drawings

OTHER PUBLICATIONS

Garner, C. V. and Pier, G. B., "Human Immune Response to *Pseudomonas aeruginosa* Mucoid Exopolysaccharide Vaccine", *Clinical Research*, vol. 36, pp. 456A (1988).

Stein, K. E., "Anti-Idiotypes as Bacterial Vaccines", in *Biological Applications of Anti-Idiotypes*, vol. 2, Bona C. A., Ed. CRC Press, Boca Raton, Fla., pp. 1–11 (1988).

Pier, G. B., et al., "Suppression of the Opsonic-Killing Antibody Response to *Pseudomonas aeruginosa* Mucoid Exopolysaccharide by Anti-Idiotypic Cytotoxic T Cells", *Clinical Research*, vol. 38, p. 390A (Apr., 1990).

Schreiber, J. R., et al., "Characteristics of a Pilot Anti-Idiotype Pseudomonas Vaccine; Isotype and Function of Anti-Idiotype-Induced Antibodies", *Fourth Annual North American & 1990 International Cystic Fibrosis Conference Abstract*, Arlington, Va., Oct. 3–6, 1990.

Baltimore, R. S., Antibiot. Chemotherpy, vol. 36:147–156, 1985.

Cabral, D. A., Pediatric Research, vol. 22(4):429–431, 1987.

ANTI-IDIOTYPIC MONOCLONAL ANTIBODIES FOR MUCOID *PSEUDOMONAS AERUGINOSA*, THEIR PREPARATION AND USE

BACKGROUND OF THE INVENTION

The present invention relates generally to infectious diseases and antibodies, and, more particularly, to a new hybridoma cell line for production of anti-idiotypic monoclonal antibodies directed to an opsonic monoclonal antibody specific to mucoid exopolysaccharide of *Pseudomonas aeruginosa*.

DESCRIPTION OF RELATED ART

Mucoid strains of *Pseudomonas aeruginosa* are the primary pulmonary pathogen for cystic fibrosis (CF) patients. Acquisition of this organism in the lungs is invariably associated with clinical decline, and there is a strong association between expression of the mucoid phenotype and growth in the lungs of CF patients. Mucoid exopolysaccharide (MEP), the primary constituent of the extracellular slime coat of mucoid strains, appears to be an important antigen in the pathophysiology of *P. aeruginosa* infection of CF patients. MEP expression promotes adherence of mucoid *P. aeruginosa* to tracheal cells and to respiratory mucins and antibodies to MEP are important to host defenses against the organism. According to earlier work (see Pier, G. B., et al., *N. Engl. J. Med.* 1987; 317: 793–798) induction of opsonic antibodies to MEP will probably be an important property of vaccines considered as candidates for prevention of mucoid *P. aeruginosa* infection in CF patients. Most CF patients respond to infection with high titers of nonopsonic antibody to MEP, and these antibodies fail to prevent progression of the infection. However, a small number of older (>12 years) CF patients have opsonic antibodies to MEP, are not infected with *P. aeruginosa*, and have an overall better clinical status. Furthermore, opsonic antibodies protect experimental animals from chronic mucoid *P. aeruginosa* lung infections. Pier, G. B., et al., *Science* 1990; 249: 537–540, the contents of which are incorporated herein by reference.

Recently, it has been observed that the heteropolymeric nature of MEP results in the presence of both common and type-specific epitopes. In addition, the common epitopes are further divided into those that bind opsonizing antibodies and those that bind nonopsonizing antibody. Most naturally occurring antibodies to MEP function poorly in in vitro opsonophagocytic assays with complement, and are unable to protect animals following intratracheal challenge with bacteria encased in agar beads. By contrast, antibodies that are highly opsonic protect animals against infection and are found among some older CF patients who are not colonized with *P. aeruginosa*. Opsonizing antibodies to MEP are usually not found in younger noncolonized or chronically colonized CF patients. These findings have suggested a protective effect for the opsonizing antibodies. It is believed that opsonizing antibodies to the MEP antigen will generally protect animals, including humans, livestock, and mammals generally, from infection. MEP has become a promising vaccine candidate for the prevention of infection with *P. aeruginosa* in CF patients. Unfortunately, MEP appears to be poorly immunogenic in humans for the induction of opsonic antibodies. MEP does not readily elicit opsonic antibodies either during chronic infection or after vaccination.

Alternative strategies to immunization with purified bacterial polysaccharides include the use of polysaccharide-protein conjugates and anti-idiotypic antibodies as substitute antigens. Anti-idiotypes directed to the antigen binding site of other antibodies may function as "internal images" of antigen and induce antigen-specific antibodies in animals without exposure to nominal antigen. See Stein, K. E., Anti-idiotypes as bacterial vaccines. In: *Biological Applications of Anti-idiotypes II.* Bona, C. A. ed. pp. 2–11, CRC Press, 1988, which is incorporated herein by reference. In addition, since anti-idiotypes are proteins, they are potentially more immunogenic than polysaccharides, particularly in young children. Anti-idiotypes have been used to induce antibodies to capsular polysaccharides and thus provide immunity to several bacterial pathogens including *Escherichia coli* (Stein, K. E., and Soderstrom, T., *J. Exp. Med.* 1984; 160:1001, incorporated herein by reference) and group C *Neisseria meningitidis* (Westerink, M. A. J., et al., *Infect. Immun.*, 1988; 56:1120–1127, incorporated herein by reference). An anti-idiotype that is a functional mimic of the immunotype-1 (IT 1) LPS O side chain of *P. aeruginosa* is capable of generating protective antibodies in syngeneic mice (Schreiber, J. R., et al., *J. Immunol.*, 1990; 144:1023–1029, incorporated herein by reference). The present invention characterizes another monoclonal anti-idiotype directed to an opsonic murine monoclonal antibody to MEP.

SUMMARY OF THE INVENTION

The present invention provides a monoclonal anti-idiotypic antibody which induces protective immunity in animal models. All experimental data to date, including animal testing, indicates that it can be used as a vaccine to generate protective immunity and prevent infections in humans, livestock, animals, and mammals in general. It would be of particular use to humans suffering from cystic fibrosis, burn patients, and those suffering from cancer. It can be used as the base for immunodiagnostics, including immunodiagnostic methods, testing, and reagents, to detect antibodies in humans and other animals and mammals. The monoclonal antibody of the present invention performs or acts as a molecular mimic of the MEP antigen of *P. aeruginosa*.

Initially, a murine monoclonal anti-idiotypic antibody directed to an opsonic monoclonal antibody (MAb) specific to MEP was produced. This anti-idiotypic MAb bound to F(ab')$_2$ fragments of the opsonic MAb, and blocked binding of the opsonic MAb to MEP. The murine anti-idiotype also bound to human opsonic antibodies from individuals immunized with MEP vaccine, providing additional evidence for the antigen-binding-site specificity of the anti-idiotype, as well as the presence of cross-reactive idiotopes on human and murine opsonic antibodies to MEP. In addition, the anti-idiotype induced MEP-specific (primarily of the IgM class) antibodies in syngeneic mice. In allogeneic mice, both IgM and IgG$_1$ antibodies to the anti-idiotype were elicited; these antibodies fixed complement onto the bacterial surface and opsonized mucoid *P. aeruginosa* for uptake and phagocytic killing by human peripheral blood leukocytes. These studies demonstrate the utility of anti-idiotypic MAb for generating protective immunity against mucoid strains of *P. aeruginosa*.

DESCRIPTION OF THE PREFERRED EMBODIMENT

EXAMPLE I

1. Materials and Methods

A. Bacterial strains and antigens

Mucoid *P. aeruginosa* strain 2192, a clinical isolate from the sputum of a patient with CF, was used as the target organism in phagocytic assays and complement deposition assays and as a source of purified MEP. MEP was purified as previously described. Garner, C. V., et al., *Infect. Immun.* 1990; 58:1835-1842, incorporated herein by reference. In the Example herein, smaller sized polymers of MEP ($K_{av}$ on a Sepharose CL4B column of <0.3) were used in ELISA and moderate sized polymers ($K_{av}=0.1-0.3$) were used for immunizing animals.

B. Preparation of opsonic MAb to MEP

Production of opsonic MAb1 directed to *P. aeruginosa* MEP was accomplished by standard techniques. Spleens from mice immunized with live mucoid *P. aeruginosa* organisms were fused with myeloma cell line SP2/O-Ag14 and wells with growth following hypoxanthine-aminopterin selection screened against purified MEP in an ELISA, as previously described. (Bryan, L. E., et al., *J. Clin. Microbiol.* 1983; 18:276-282 and Pier, G. B., et al., *J. Clin. Microbiol.* 1986; 24:189-196, both incorporated herein by reference). Cells in wells positive for antibody to MEP were cloned twice by limiting dilution, and the antibodies were tested for opsonic activity in a phagocytic assay described below. Two positive clones secreting $IgG_{2b}$ antibodies were used in the experiments reported here.

C. Preparation of the anti-idiotypic MAb

The anti-idiotypes were made by immunizing 8-wk.-old BALB/cByJ mice subcutaneously (sc) with 10 ug of the opsonic anti-MEP MAb (MAb1) in complete Freund's adjuvant and then with 10 ug MAb1 in incomplete Freund's adjuvant twice per week for 4 weeks. Anti-idiotype-induced seroconversion to MAb1 was documented by ELISA screening (see below) using F(ab')$_2$ fragments from MAb1. The spleen of one mouse was then obtained 72 hours after the final immunization and used for production of hybridomas. Hybridomas were produced via fusion with the SP2/O mouse myeloma cell line, screened by ELISA for production of anti-idiotype antibodies, and then cloned by repeated limiting dilution. Anti-idiotypic antibodies were purified from ascites fluid of pristane-primed BALB/cByJ mice by passage over a protein A-Sepharose column (Pharmacia Fine Chemicals, Piscataway, N.J.), as described in Schreiber, J. R., et al., *J. Immunol.* 1990; 144:1023-1029, incorporated herein by reference. One clone, C9F5, was found to be stable and to produce large quantities of antibody of the IgG2a isotype; it was used for further experiments.

D. Induction of MEP-specific antibodies in mice by immunization with anti-idiotypic MAb To determine whether MEP-specific antibodies could be induced in 8-wk.-old syngeneic BALB/cByJ mice, the animals were immunized intraperitoneally (ip) or sc with 20- ug doses of anti-idiotype MAb C9F5 without adjuvants. The immunization schedule was either two doses separated by three weeks or one dose per week for 4 weeks. In order to determine whether antibodies to MEP could be induced in allogeneic C3H/HeN mice, these animals were immunized with varying doses (0.5-50 ug) of the C9F5 anti-idiotype weekly for 4 weeks. Serum was obtained weekly from all mice by tail vein bleeding, pooled and screened for binding to MEP by ELISA. Control animals received an irrelevant MAb of the same isotype by the same method of administration as the anti-idiotypic MAb C9F5 (IgG2a anti-Sendai virus kindly supplied by Drs. John Nedrud and Mary Mazanec, Case Western Reserve University School of Medicine, Cleveland, Ohio). For purposes of comparison, some animals received 1-ug doses of purified MEP antigen.

E. ELISA for detection of antibodies

Supernates from clones or mouse sera were screened for anti-idiotypic antibodies in an ELISA using plates sensitized with F(ab')$_2$ fragments from the anti-MEP MAb1. The F(ab')$_2$ fragments were prepared as described in Schreiber, J. R., et al., *J. Immunol.* 1990; 144:1023-1029, and Lamoyi, E., et al., *J. Immunol. Methods* 1983; 56:235-243, incorporated herein by reference. Each F(ab')$_2$ preparation was screened for purity by an ELISA with goat anti-mouse IgG Fc-specific antibodies conjugated to alkaline phosphatase (AP), and by SDS-PAGE. ELISA plates were coated with 100 ul/well of F(ab')$_2$ fragments (2.5 ug/ml concentration), then blocked with PBS containing 1% BSA for 60 minutes. After washing, sera or supernates were added, followed by goat anti-mouse IgG Fc fragment-specific or anti-mouse IgM, u-chain specific AP conjugates (Cappel Antibodies, Westchester, Pa.). The ELISA was developed with phosphatase substrate (1 mg/ml in diethanolamine, 0.5 mM $MgCl_2$, 0.02% sodium azide, pH 9.8 [DEA buffer], Sigma, St. Louis, Mo.). Plates were read at 410 nm with a Titertek Multiscan ELISA plate reader (Flow Laboratories, Mclean, Va.).

Sera or tissue culture supernates were screened for MEP-specific antibodies by coating ELISA plates with 100 ul/well of 2.5 ug tyraminated MEP/ml. Tyramination was performed as described in Schreiber, J. R., et al., *J. Immunol.* 1990; 144:1023-1029, with cyanogen bromide coupling and was found to enhance binding of MEP to the ELISA plates. After blocking with 1% BSA in PBS, serum or tissue culture supernate was added. IgG, IgM, or IgA antibodies to MEP were detected with AP-conjugated, class- and subclass-specific goat anti-mouse Ig (Southern Biotech, Birmingham, Al.). Plates were developed as described above. Specificity of antibody to MEP in sera or tissue culture supernates was confirmed by preincubating these specimens with MEP (100 ug/ml) and observing inhibition of antibody binding to solid phase MEP in the ELISA.

Blocking of binding of MAb1 to MEP by anti-idiotype was determined with use of ELISA plates coated with the tyraminated MEP described above. Plates were blocked with BSA, washed, and then incubated with MAb1 that had been mixed either with various concentrations of the C9F5 anti-idiotype or the control MAb of the same isotype and concentrations. The concentration of MAb1 was chosen because it had previously been determined to be on the linear part of a titration curve in the ELISA. Plates were washed, monoclonal anti-mouse $IgG_{2b}$ AP conjugate was added (Southern Biotech); standard procedures were then followed. The percentage inhibition of MAb binding to MEP-coated ELISA plates by the anti-idiotype was calculated as follows: % inhibition=[1−[absorbance with anti-idiotype/absorbance without anti-idiotype]]×100.

F. Complement Binding Assay

Fresh human serum as a source of complement was obtained from volunteers and stored at −80° C. Purified C3 was kindly provided by Dr. Margaret Hostetter, University of Minnesota. This preparation showed only two bands in SDS-PAGs corresponding to the α and β chains of C3. C3 was labeled with $^3H$ by reductive methylation using the method described in Tack et al., *J. Biol. Chem.*, 1980; 255:8842–8847, incorporated herein by reference. A specific activity of 325 cpm/ng was achieved. Bacteria ($10^8$ cfu from a log phase culture) were opsonized with 1:8 dilutions of murine sera that were heat-inactivated. Bacteria and sera were incubated for 5 minutes in the presence of 0.5% (final concentration) fresh human serum and 11.5 ug of $^3H$-labeled C3. After opsonization, bacteria were washed three times in PBS containing 1% SDS to remove non-covalently associated C3 and the cpm bound to the bacteria were measured in a scintillation counter. Parallel studies indicated no measurable loss in viability of mucoid *P. aeruginosa* cells washed under these conditions. The number of C3 molecules covalently bound per organism was calculated with the formula described in Hostetter, M. K., *J. Infect. Dis.* 1986; 153:682–693, incorporated herein by reference.

G. Detection of binding of anti-idiotypic MAb to human antibodies to MEP

Adult volunteers with pre-existing nonopsonic antibody to MEP were immunized with 100 ug of an MEP vaccine as described in Garner, C. V., et al., Clin. Res. 1988; 36:465A. The MEP-specific antibodies from pre- and post-vaccination sera of four individuals who responded with opsonic antibody to MEP were then isolated by affinity chromatography, using a column of epoxy-activated Sepharose coupled to purified MEP. From these preparations, the IgG fraction was obtained by chromatography on protein A Sepharose. Fab fragments were prepared from these antibodies by incubating the affinity-purified material with papain immobilized on Sepharose. The digests were again passed over a protein A column to remove undigested antibody and Fc fragments. Characterization of the preparations by SDS-PAGE revealed no intact heavy chains. ELISA plates were coated with 1 ug of affinity-purified human antibody or Fab fragments in carbonate-bicarbonate buffer, pH 9.6. After sensitization for 2 hours at 37° C., the plates were washed and blocked with 5% skim milk in PBS, and the protein A purified anti-idiotypic MAb C9F5 was added. After another 2 hours at 37° C., the plates were washed, and AP-conjugated goat anti-mouse IgG diluted in PBS with 0.05% tween, 5% skim milk, and 2% normal human serum was added. After 2 more hours at 37° C., the plates were washed, and paranitrophenol phosphate in 0.1M carbonate buffer containing 100 mg/L of $MgCl_2$ was added. Absorbance was read after 60 minutes at 405 nm.

H. Measurement of opsonic activity of anti-idiotype-induced MEP-specified antibodies Murine antisera raised to anti-idiotype MAb C9F5, or control serum raised against 1 ug of MEP, were assessed for opsonic activity as described in Ames P. et al., *Infect. Immun.* 1985; 49:281–285, incorporated herein by reference. Briefly, heat-inactivated serum (1:8 dilutions) were mixed with $2 \times 10^6$ cfu of mucoid *P. aeruginosa* strain 2192, $2 \times 10^6$ fresh human leukocytes (obtained from dextran sedimentation of whole blood) and 2% fresh human serum as a complement source. Samples were obtained at the beginning and end of a 90-minute incubation period at 37° C., diluted, and plated for bacterial enumeration. Each sample was run in duplicate, and the contents of each tube were plated in duplicate. Results are expressed as the mean value of the four determinations per sample.

2. Results

A. Production of anti-idiotype serum and MAb

Several immunization regimens were employed to induce circulating anti-idiotype antibodies in BALB/cByJ mice. Twice weekly administration of 10 ug of anti-MEP MAb1 initially with complete Freund's adjuvant and then with incomplete Freund's adjuvant, consistently produced seroconversion by week 4 as determined in the ELISA with F(ab')$_2$ of anti-MEP MAb1 as coating antigen. Seven hybridomas from fusion experiments were found to produce anti-idiotypic antibodies. One stable hybridoma was cloned repeatedly by limiting dilution and was chosen for further experiments (C9F5, IgG2a subclass). The specificity of antibodies from this clone was measured by coating microtiter wells with F(ab')$_2$ fragments from the anti-MEP MAb1, adding the C9F5 antibody, and then using an AP-conjugated goat anti-mouse IgG Fc-specific antibody as described in *Materials and Methods*. The C9F5 anti-idiotype bound to F(ab')$_2$ of anti-MEP MAb1 in a dose-dependent fashion. The anti-idiotype did not bind to F(ab')$_2$ fragments from other murine MAbs, and the control MAb of the same isotype as the anti-idiotype did not bind to the anti-MEP MAb1 F(ab')$_2$ fragments.

B. Blocking of anti-MEP MAb1 binding to MEP by the anti-idiotype

To determine whether the anti-idiotype structurally resembled MEP, microtiter plates were coated with tyraminated MEP, and anti-MEP MAb1 that had been incubated with various quantities of anti-idiotype was added. Anti-idiotype inhibited binding of the anti-MEP MAb1 to MEP in a dose-dependent manner. By contrast, a control antibody of the same isotype and quantity as the anti-idiotype did not inhibit binding of anti-MEP MAb1 to antigen in a dose-dependent fashion. These findings suggested that the C9F5 anti-idiotypic MAb functioned in vitro as a molecular mimic of MEP.

C. Binding of the anti-idiotypic MAb to human antibodies to MEP

Immunization of humans with MEP resulted in production of opsonic antibody in about 20% of the vaccinees, Garner, C. V. and Pier, G. B., Clin. Res., 1988; 36:465A. Whether anti-idiotype C9F5 bound to intact, affinity-purified antibodies to MEP and their Fab fragments coated onto ELISA plates was tested, using the preimmunization sera from four of these individuals as a source of nonopsonic antibody and the postimmunization sera as a source of opsonic antibody. Intact opsonic antibodies from all four individuals bound the anti-idiotype, as did Fab preparations from three of four individuals. None of the nonopsonic preparations bound to the anti-idiotype. Further studies showed that, in the presence of purified MEP (100 ug/ml), the anti-idiotypic MAb did not bind to the opsonic antibody preparations.

D. Induction of anti-MEP antibodies in syngeneic BALB/cByJ mice with anti-idiotypic MAb Since the C9F5 anti-idiotype bound to F(ab')$_2$ of murine anti-MEP MAb1 as well as to human opsonic antibodies and Fab fragments in a manner suggestive of molecular mimicry of MEP, whether administration of anti-idiotype to syngeneic mice would elicit antibodies to MEP was investigated. Seven BALB/cByJ mice were injected with 20 ug of anti-idiotypic MAb or control antibody in two doses given 3 weeks apart or in one dose per week for 4 weeks. Each mouse was bled weekly to determine the presence of antibodies to MEP as measured by binding to tyraminated-MEP-coated ELISA plates. Previous experiments had determined that 20 ug of the anti-idiotypic MAb yielded the highest antibody response to MEP. Administration of the anti-idiotypic MAb by these two schedules yielded anti-MEP antibody of the IgM class by day 7 post-immunization. Higher titers were obtained with repetitive doses, but the antibody remained solely of the IgM class. Control animals immunized with four weekly 20-ug doses of an IgG$_{2a}$ antibody against Sendai virus made no antibody response to MEP. BALB/cByJ mice given 10 ug of purified MEP antigen produced a detectable antibody response to MEP within 7 days of immunization, as has been previously described in Garner, C. V., et al., *Infect. Immun.* 1990; 58:1835–1842. Both IgM and IgG3 antibodies were detected, a finding consistent with previous reports of the isotypically restricted murine antibody response to purified polysaccharides. (Perlmutter, R., et al., *J. Immunol.* 1978; 121:566–572)

E. Induction of antibodies to MEP in allogeneic C3H mice by anti-idiotype MAb Anti-idiotypic MAb C9F5 administered in doses of 0.5–50 ug to allogeneic C3H/HeN mice resulted in production of antibodies to MEP. As with the BALB/cByJ mice, anti-idiotypic MAb given once per week for 4 weeks induced detectable IgM antibodies at most of the doses 7 days after the initial immunization. These IgM antibodies tended to decline after this initial period. In contrast to the results in syngeneic BALB/cByJ mice, IgG$_1$ antibodies to MEP were elicited in the C3H/HeN mice by week 3 when doses of the anti-idiotypic MAb of $\geq 10$ ug were used, and by week 4 when doses of 0.5 and 1 ug were given. IgG$_1$ is the murine isotype commonly associated with immune responses to protein antigens. Anti-idiotypic MAb C9F5 is a protein.

F. Opsonic ability of the anti-idiotype-induced antibodies to MEP

Next, whether the antibodies induced by the anti-idiotypic MAb could opsonize mucoid *P. aeruginosa* for killing by human leukocytes was addressed. C3H/HeN mice were iummunized once per week for 4 weeks with 0.5 to 50 ug of the anti-idiotype MAb C9F5. Killing of mucoid *P. aeruginosa* strain 2192 was assessed after 90 minutes in an opsonophagocytic assay by a 1:8 serum dilution. Serum obtained 3 to 4 weeks after immunization with the anti-idiotypic MAb led to peripheral blood leukocyte killing of >80% of mucoid *P. aeruginosa*. Development of opsonizing antibody was coincident with the appearance of IgG$_1$. Serum from control mice immunized with 1 ug of MEP once per week for 4 weeks also produced opsonophagocytic killing 3 weeks after the initial dose. No phagocytic killing was observed if complement, antibody or phagocytic cells were omitted from the assay. Serum obtained from BALB/cByJ mice immunized with anti-idiotype was poorly opsonic, perhaps due to restriction of the response to the IgM isotype.

G. Fixation of complement to the surface of mucoid *P. aeruginosa* by the anti-idiotype-induced, MEP-specific antibodies Whether the anti-idiotype-induced MEP-specific antibodies could fix complement to the bacterial surface was addressed. Deposition of the third component of complement onto antibody-opsonized mucoid *P. aeruginosa* was studied. Bacteria were incubated for 5 minutes with sera from C3H/HeN mice, $^3$H-labeled C3, and 0.5% intact human serum as a complement source. C3 binding was detected by scintillation counting following washing in 1% SDS in PBS. Sera from C3H mice immunized with 4 weekly doses of 10–50 ug of C9F5 anti-idiotype showed that by day 21 post-immunization there was about a 10-fold increase in the number of molecules of C3 per cfu. This level of C3 deposition was comparable to that obtained by immunizing with 1 ug of MEP. Lower (0.5 and 1 ug) amounts of the anti-idiotypic MAb achieved a 10-fold increase in molecules of C3 per cfu after the fourth immunization.

3. Discussion

MEP, the major constituent of the slime that coats mucoid *P. aeruginosa*, appears to play a role in the ability of these mucoid bacteria to infect the lungs of CF patients. MEP may facilitate persistence of the organism in the lungs by blocking proper attachment of antibodies or complement. In addition, MEP is a heteropolymer, and antibodies to MEP may be directed to epitopes that do not promote efficient bacterial clearance via opsonophagocytic killing. Furthermore, antibodies of different isotypes, even when directed at the same epitope, may have different functional characteristics, some being deficient in opsonic activity. This phenomenon was seen here where the development of opsonic activity was associated with the appearance of IgG$_1$, but not IgM, antibodies. Human trials with a purified MEP vaccine have demonstrated a disappointing opsonophagocytic-killing antibody response.

The present specification describes an anti-idiotypic antibody to an opsonizing MAb specific to MEP that immunologically mimics MEP in both in vitro and in vivo assays. The anti-idiotypic antibody binds to F(ab')$_2$ fragments from the opsonic anti-MEP MAb1, blocks binding of the same anti-MEP MAb1 to MEP, elicits MEP-specific antibodies in syngeneic and allogeneic mice, and binds to opsonic human antibodies obtained from MEP-vaccinated volunteers. Thus, these data support the belief that the anti-idiotypic MAb C9F5 functions as a molecular mimic of MEP. It is clear that anti-idiotypes can elicit antigen-specific antibody responses in vivo in the absence of actual native antigen.

Syngeneic BALB/cByJ mice receiving the C9F5 anti-idiotypic mimic of MEP made an isotypic response restricted to IgM antibodies. Such a restricted isotypic response resembles that seen to native polysaccharide antigens in which T cell help is presumably minimal. It seems possible that in the syngeneic system anti-idiotypes are seen primarily as "self" antigens poorly able to recruit T cell help.

The antibodies to MEP induced in allogeneic C3H mice by the anti-idiotype were of both IgM and IgG$_1$ isotypes. IgG1 subclass responses in mice are often elicited against T cell-dependent protein antigens. Since C3H mice differ from BALB/cByJ mice in MHC haplotype (H2$^k$ vs. H2$^d$ respectively), it is possible that presentation of the anti-idiotype in this allogeneic system recruits T-cell help and an expansion of isotypes of the MEP-specific antibodies. The development of IgG antibodies in these studies is consistent with previous observations that development of IgG antibodies to opsonic epitopes on MEP is required for maximal phagocytic killing.

Of critical importance was the observation that the anti-idiotype-induced, MEP-specific antibodies elicited in allogeneic mice fixed complement to the bacterial surface and had opsonic activity against mucoid *P. aeruginosa*.

It is believed that additional testing and screening in accordance with the procedures and techniques disclosed herein may be used to produce and isolate additional cell lines which produce antibody having similar qualities, characteristics and effectiveness as those disclosed herein.

Hybridoma C9F5, described herein, was deposited with the American Type Culture Collection (ATCC), 12301 Parklawn Drive, Rockville, Md. 20852, U.S.A., on Apr. 3, 1991, and has been given the ATCC designation or accession number, HB 10715. The deposit was made and accepted under the provisions of the Budapest Treaty. All restrictions upon public access to the deposit will be irrevocably removed upon the grant of a patent on this application, and the deposit will be replaced if viable samples cannot be dispensed by the depository.

C9F5 can be cultivated in RPMI medium with 25,000 U Penicillin/streptomycin, 1.0 ml 2ME ($5 \times 10^{-5}$), 10% endotoxin free fetal bovine serum, 5.0 ml of 200 millimolar L-glutamine.

It has been shown that the C9F5 anti-idiotype generates protective immunity in mice, and that it works as a vaccine in mice. All data collected to data indicate that C9F5 will be efficacious in generating protective immunity to mucoid *P. aeruginosa* in humans and animals. Thus, it is believed that C9F5 anti-idiotype, as a vaccine, will generate protective immunity and prevent infections from mucoid *P. aeruginosa* in humans, livestock, and animals. A vaccine induces protective immunity. A vaccine, when inoculated into or administered in an effective amount to the host, prevents infection by inducing production of protective antibodies and protective memory cells. The protective antibodies so produced can be collected and used as part of an immune or hyperimmune globulin. Such an immune or hyperimmune globulin can be passively administered to an individual in need of these protective antibodies.

To inoculate a human with C9F5 anti-idiotype, it is believed that the proper dosage is about 50–100 ug, preferably about 100 ug, injected subcutaneously, generally in sterile saline or comparable solution. Typically, there would be two injections, one primary and one booster, separated by 4 to 8 weeks. Typically, the same amount is given in each injection. Vaccination techniques and methodologies are known in the prior art, or may be readily adapted by one skilled in the art to enable use with the novel antibodies herein. The disclosures of U.S. Pat. Nos. 4,693,891 and 4,160,023 are incorporated herein by reference in their entirety. For effective treatment, it may be necessary to link the C9F5 to a carrier such as to conjugate the C9F5 anti-idiotype to another protein to enhance its immunogenicity, such as by covalent linkage to diphtheria toxoid or Pseudomonas exotoxin A. Covalent linkage to diphtheria toxoid and exotoxin A is known in the prior art. To those skilled in the art, similar inoculation techniques and dosage levels and schedules, based on experimental results, known proportions, ratios, and tendencies, would be utilized for inoculations in livestock and other animals.

A "pharmaceutical preparation" is used herein in its broader sense to include preparations containing a composition or antibody in accordance with the invention used not only for therapeutic or inoculation purposes, but also for reagent purposes as are known in the art or for tissue culture purposes. If the pharmaceutical preparation is to be employed as a reagent, then it should contain reagent amounts of composition or antibody. Similarly, when a pharmaceutical preparation is used in tissue culture or a tissue culture medium, it should contain amounts sufficient to obtain the desired growth.

A pharmaceutically-acceptable carrier, in the inoculation or immunization art, may be with or without pharmaceutically-acceptable adjuvant. As the carrier, one may use distilled water, physiological saline and phosphate-buffered aqueous sodium chloride solution. Illustrative of adjuvants are aluminum hydroxide, aluminum phosphate, calcium phosphate, alum, and Freund's incomplete adjuvant. The amount of adjuvant may be appropriately selected from the range of amounts being necessary and sufficient for increasing the immuno-activity.

C9F5 anti-idiotype can also be used as a substitute for MEP antigen for diagnostic purposes, such as detecting the presence of antibody in a specimen. For example, C9F5 anti-idiotype can be substituted for purified MEP antigen on an ELISA plate to detect anti-MEP antibody. C9F5 antibody can be coated onto or bound onto a substrate such as an ELISA plate. The specimen containing the antibody to be detected, such as anti-MEP antibody, is placed in contact with the bound C9F5. Anti-MEP antibody in the specimen then binds to the C9F5. Detection means are then employed to detect the presence of bound anti-MEP antibody. The procedure can also be reversed, whereby the specimen containing the antibody to be detected is applied to the ELISA plate first, and the C9F5 antibody is applied thereafter. Alternatively, the specimen can be bound to the substrate, such as nitrocellulose paper in a Western Blot, where the antibody to be detected can be separated out by such techniques as gel electrophoresis. A solution containing C9F5 antibody is then applied to the paper; the C9F5 binds to the bound antibody of interest and is then detected. Alternatively, radioactively-labeled C9F5 can be used using known techniques. The procedures and manipulative steps and techniques to be employed in these diagnostic methods correspond with those described herein or may be readily adapted or utilized by one skilled in the art to enable use with the novel antibodies herein.

It is believed that C9F5 will act much more specifically as a detector on such things as an ELISA plate than purified MEP antigen, since purified MEP typically is somewhat non-specific and binds to a greater variety of antibodies than does C9F5, including MEP antibodies that are nonopsonic and non-protective. C9F5 only binds to protective, opsonic antibodies and is thus a better measure of *Pseudomonas immunity*. The use of C9F5 anti-idiotype as a substitute for purified MEP antigen, both as a vaccine and as a diagnostic tool or probe, also has the advantage that the workers are working with and handling a non-toxic, essentially non-harmful protein such as C9F5, rather than working with, grinding up, handling, etc., the potentially pathogenic and hazardous mucoid *P. aeruginosa* bacteria. The safety of the workers is thus enhanced. It would also be much cheaper to use C9F5 anti-idiotypes, since they can be cheaply grown up in large quantities and more easily purified. Purified MEP is more expensive both to produce and purify.

C9F5 anti-idiotype, since it is monoclonal, can be used as a specific probe, using ELISA screening techniques, to determine how similar CF patients are, in that it can be determined whether different CF patients have raised up similar, or different, antibodies to mucoid *P. aeruginosa*. The C9F5 anti-idiotype would act as a probe for the heterogeneity of the variable region of the antibody to MEP. Determining the similarity or dissimilarity of CF patients, in the similarity or dissimilarity of their antibodies to *P. aeruginosa*, can be useful for diagnostic and research purposes.

While the invention has been shown and described with respect to one or more particular embodiments thereof, this is for the purpose of illustration rather than limitation, and other variations and modifications of the specific embodiments herein shown and described will be apparent to those skilled in the art all within the intended spirit and scope of the invention. Accordingly, the patent is not to be limited in scope and effect to the specific embodiments herein shown and described nor in any other way that is inconsistent with the extent to which the progress in the art has been advanced by the invention.

What is claimed is:

1. An anti-idiotypic monoclonal antibody or a binding fragment thereof, said monoclonal antibody or binding fragment thereof being produced by the cell line designated C9F5 and having ATCC Accession No. HB 10715 or a subclone thereof having all the properties and characteristics of the cell line having ATCC Accession No. HB 10715.

2. A composition comprising an anti-idiotypic monoclonal antibody or binding fragment thereof according to claim 1, and an acceptable carrier.

3. The cell line designated C9F5 and having ATCC Accession No. HB 10715 or a subclone thereof having all the properties and characteristics of the cell line having ATCC Accession No. HB 10715.

* * * * *